United States Patent [19]
Vaillancourt

[11] Patent Number: 5,356,379
[45] Date of Patent: Oct. 18, 1994

[54] DISPOSABLE AMBULATORY INFUSION PUMP ASSEMBLY

[76] Inventor: Vincent L. Vaillancourt, 14 Bunyan Dr., Livingston, N.J. 07039

[21] Appl. No.: 100,978
[22] Filed: Aug. 3, 1993
[51] Int. Cl.⁵ ............................................. A61M 5/14
[52] U.S. Cl. ..................................... 604/80; 604/131
[58] Field of Search ....................... 604/80, 82, 86, 89, 604/131, 133, 246, 258

[56] References Cited

U.S. PATENT DOCUMENTS

| | | | |
|---|---|---|---|
| 4,294,249 | 10/1981 | Sheehan et al. | 604/86 |
| 4,424,056 | 1/1984 | Urquhart et al. | 604/85 |
| 4,909,790 | 3/1990 | Tsujikawa et al. | 604/132 |

Primary Examiner—Jerome L. Kruter
Attorney, Agent, or Firm—Francis C. Hand

[57] ABSTRACT

The disposable ambulatory infusion pump assembly includes a line through which there is a restricted flow of fluid from a pump to a T- or Y-Site connector. The flow is sufficient to keep the vein of a patient opened, for example, using a flow rate of 0.5 cubic centimeters per hour. A second line is disposed in parallel to the first line to convey fluid from the pump to the T-connector at a higher flow rate and a clamp is provided for opening and closing the second line. Opening of the clamp permits the line to the T-connector to be primed when desired. Opening of the clamp also permits flushing of the T-connector and following lines after injection of a medication dose through the injection port of the T-connector. A restrictor may also be disposed in the line with a valve actuator to move the restrictor from a valve seat in the line to allow a greater flow of fluid about the restrictor than through the restrictor.

14 Claims, 2 Drawing Sheets

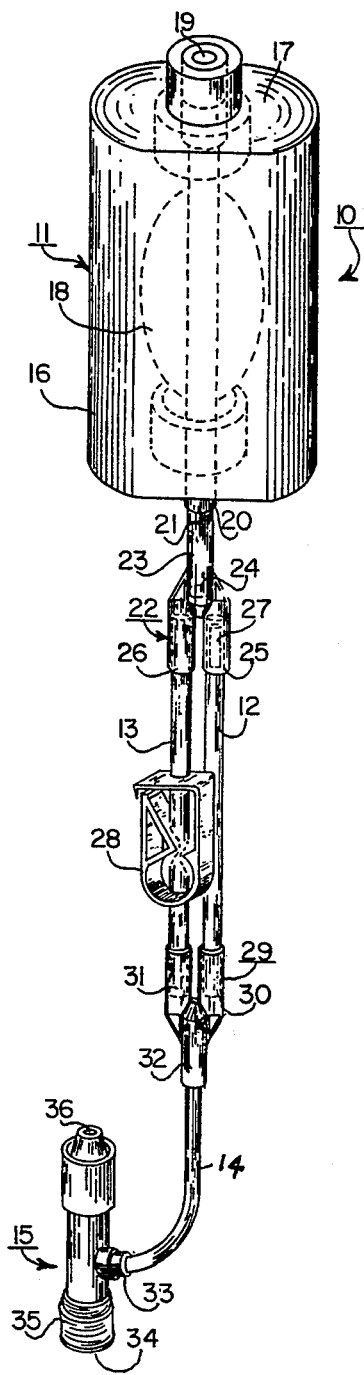
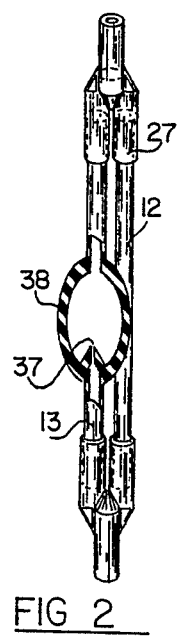
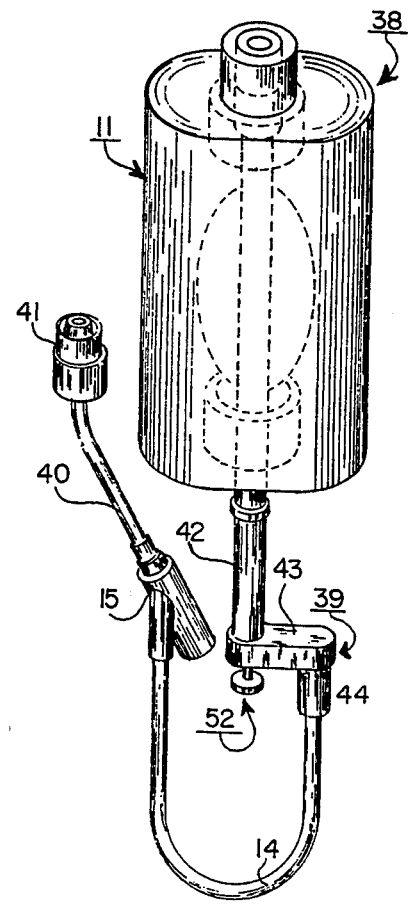
FIG 1
FIG 2
FIG 3

DISPOSABLE AMBULATORY INFUSION PUMP ASSEMBLY

FIELD OF INVENTION

This invention relates to a disposable ambulatory infusion pump assembly. More particularly, this invention relates to an infusion pump assembly and a method for delivering fluid intravenously to a patient.

DESCRIPTION OF RELATED ART

As described in U.S. Pat. No. 5,059,174, various techniques have been used for infusing medications, drugs and the like into a patient from time to time, for example, using a procedure often known as SASH. In addition, techniques have also been known which avoid the need for a SASH procedure by using an ambulatory disposable infusion delivery system as described in U.S. Pat. No. 4,867,743. In such a case, a small infusion device is used to feed a small continuous flow of physiological saline solution into a catheter placed in a patient. This continuously infused solution is to prevent occluding of the catheter and may employ a restrictor in the fluid line so that the flow rate can be predicted for a given fluid.

Other types of ambulatory disposable infusion delivery systems have also been known such as described in U.S. Pat. No. 4,813,937 which employ a housing with a piston movable under the force of a stretched elastomeric member and a restrictor in a delivery line in order to delivery medication from the housing in a controlled amount.

Still other types of infusion devices have been known which employ an elastomeric bladder for receiving liquid under pressure and a line which extends from the bladder with a restrictor therein for controlling the flow rate of fluid through the line. Such devices are described in U.S. Pat. Nos. 5,080,652; 4,909,790 and 4,904,239.

Other devices have also been known for regulating a flow from a dispensing device, such as by using a relatively long capillary tubing as a delivery line, such as described in U.S. Pat. No. 4,597,754.

Still another system has been described in U.S. Pat. No. 5,188,603 using a primary pump to infuse a medicament into an implanted catheter in a vein and a secondary pump to infuse a saline solution into the catheter to keep the vein open after the medicament has been infused.

Devices have also been known such as described in U.S. Pat. No. 5,011,477 for delivering a bolus dose into a patient by maintaining a constant flow rate of a beneficial agent into a patient and, from time to time, charging a bolus dose of the beneficial agent into the line. To this end, a dose reservoir is provided which receives a dose of the beneficial fluid from the same source as the fluid passing into a patient at a constant rate. Once the reservoir has been filled with the appropriate dose, a reservoir compression means is activated by the patient in order to charge the bolus dose into the line leading to the patient.

Devices have also been known such as described in U.S. Pat. No. 4,381,591 for continuously supplying a small flow of fluid into a patient's artery and in periodically flushing the line with a larger flow of fluid to prevent blood from backing up into a catheter.

However, none of the known devices functions as a relatively simple infusion pump assembly and in many cases, the known devices do not function as a convenient disposable ambulatory infusion pump assembly.

SUMMARY OF THE INVENTION

Accordingly, it is an object of the invention to provide a relatively simple assembly for delivering fluid intravenously to a patient.

It is another object of the invention to provide a compact infusion pump assembly which can be worn by a patient and which can be readily used to prime a line leading to a catheter.

It is another object of the invention to provide a simple disposable ambulatory infusion pump assembly for infusing a fluid medicament through a line into a patient's vein and thereafter purging the line to remove residual medicament.

Briefly, the invention provides a disposable ambulatory infusion pump assembly and a method of intravenously infusing a fluid into a patient.

In one embodiment, the infusion pump assembly includes a pump means for supplying a pressurized flow of fluid, a first line in communication with the pump means for conveying the pressurized flow of fluid thereto at a first flow rate, a second line connected in parallel with the first line for conveying a flow of fluid from the pump means at a second rate of flow higher than the first rate of flow, a third line connected in common to the first and second lines to receive a flow of fluid from each line and a connector having an inlet port connected to the third line to receive a flow of fluid therefrom and an outlet port communicating with the inlet port to discharge fluid. In addition, a means is provided in the second line for selectively opening and closing the second line to a flow of liquid therethrough. This means functions so that when the second line is opened, a flow of fluid is passed from the pump means through the second line and third line to the connector in order to prime the third line.

The connector of the pump assembly may also include a second inlet port for receiving a dose of a second fluid, such as a medicament. In this case, the second inlet port is also in communication with the outlet port so that the second fluid can be infused intravenously into the vein of a patient. With this construction, after a dose of a second fluid is passed through the connector into a patient, the second line is opened via the means therein so that a flow of fluid from the pump means passes through the second line, third line and connector in order to flush the second fluid from the outlet port of the connector.

The infusion pump assembly may employ a restrictor in one portion of the first line for restricting the rate of flow of the fluid through the line to one which is sufficient to keep a vein open. For example, the flow rate may in the range of 0.1 to 5 cubic centimeters per hour. On the other hand, the second line which is parallel to the first line may be sized to have a flow rate in the range of from 1 to 3 cubic centimeters per minute. In this respect, the flow of fluid through the second line is an unrestricted rate of flow relative to the restricted rate of flow in the first line.

The means provided in the second line for opening and closing of the line may be in the form of a clamp which may be manually manipulated, for example, by the patient.

In another embodiment, the means in the second line may include a one-way valve and an inflatable reservoir upstream of the valve for receiving fluid therein. In this embodiment, collapsing of the reservoir under an externally applied collapsing force causes the valve to open thereby permitting a flow to take place through the second into the connector.

In still another embodiment, use may be made of a single line for supplying either a restricted flow or an unrestricted flow to a patient. For example, the pump assembly may employ a purging and priming device in a line leading from the pump means wherein the device includes a means for selectively deliverying one of a restricted flow of fluid from the pump at a rate sufficient to keep a vein open and a relatively larger unrestricted flow of the fluid at a larger rate of flow. As above, the line extending from the purging and priming device is connected to an inlet port of a Y-site or "T" connector so that fluid may be conveyed to keep a vein open or fluid may be conveyed at a rate to prime the line to the patient or to purge the line to the patient from medicament which may have been delivered to a second inlet port of the Y-site connector.

In this latter embodiment, the purging and priming device employs a restrictor in the form of a tube in one portion of the line for restricting the rate of flow of fluid through the line. The restrictor is also biased against a valve seat by a spring. In addition, a second portion of the line which is parallel with the portion of the line containing the restrictor is sized to convey a flow of fluid from the pump means around the restrictor to the connector at an unrestricted rate of flow relative to the rate of flow through the restrictor. A means in the form of a valve actuator is also provided for selectively opening and closing this second portion of the line to a flow of fluid therethrough. The valve actuator also serves to move the restrictor from the valve seat.

In operation, with the restrictor biased against the valve seat, a restricted flow of fluid is delivered from the pump means to the connector and into a patient. When a dose of medicament has been delivered into the vein of a patient through the connector, the valve actuator can be activated to move the restrictor away from the valve seat so that a greater flow of fluid flushes through the line to purge the medicament from the line passing into patient.

A suitable locking means may also be provided to guard against inadvertant actuation of the purging and priming device.

The invention also provides a method of intravenously infusing a fluid into a patient. The method includes the steps of providing a source of fluid pressure, conveying a continuous flow of the fluid from the source through a flow path into a vein of the patient, restricting the flow of fluid in the flow path to effect a first flow rate sufficient to keep the vein open. In accordance with the invention, after charging a dose of medicament into the flow path downstream of the source of fluid for delivery into the vein of the patient, a second flow of fluid is conveyed from the source at a second flow rate greater than the first flow rate through the flow path in order to flush residual medicament from the flow path into the vein.

In one embodiment, a continuous flow of fluid is made in a restricted manner through a portion of the flow path in order to effect a first flow rate sufficient to keep the vein open. In accordance with the invention, a second flow of fluid is conveyed from the source of fluid at a second flow rate greater than the first flow rate through a second flow path into the first flow path downstream of the portion in which the flow of fluid is restricted in order to prime the first flow path downstream of the portion of the first flow path in which the flow is restricted.

In this embodiment, the flow rate to be affected through the first flow path may be in the range of 0.5 cubic centimeters per hour so that some time is required for the line to fill, for example, from 2 to 5 minutes. The second line in which the flow is not restricted is able to fill much more rapidly, for example, in about 15 seconds thereby filling not only the line but any connector and injection port leading from the connector. Thus, the pump assembly can be primed in a reasonable time period. After priming, the second flow of fluid can be stopped.

The method allows a medicament to be administered, for example, by a practitioner. In this case, a dose of medicament is charged into the flow path downstream of the portion in which the flow is restricted for delivering to the vein of a patient. Typically, the medicament would be administered through a connector which is connected to a line through which the restricted flow rate is continuously flowing. After administration, the second flow of fluid is caused to occur thereby flushing the remaining portion of the medicament from the connector into the vein of the patient. Thereafter, the second flow of fluid can be stopped.

DESCRIPTION OF THE DRAWINGS

These and other objects and advantages of the invention will become more apparent taken in conjunction with the accompanying drawings wherein:

FIG. 1 illustrates a view of a disposable ambulatory infusion pump assembly constructed in accordance with the invention;

FIG. 2 illustrates a modified means for opening and closing a second line of the infusion pump assembly of FIG. 1;

FIG. 3 illustrates a perspective view of a modified disposable ambulatory infusion pump assembly employing a single forward flow line in accordance with the invention;

DESCRIPTION OF THE PREFERRED EMBODIMENTS

Figure 4:
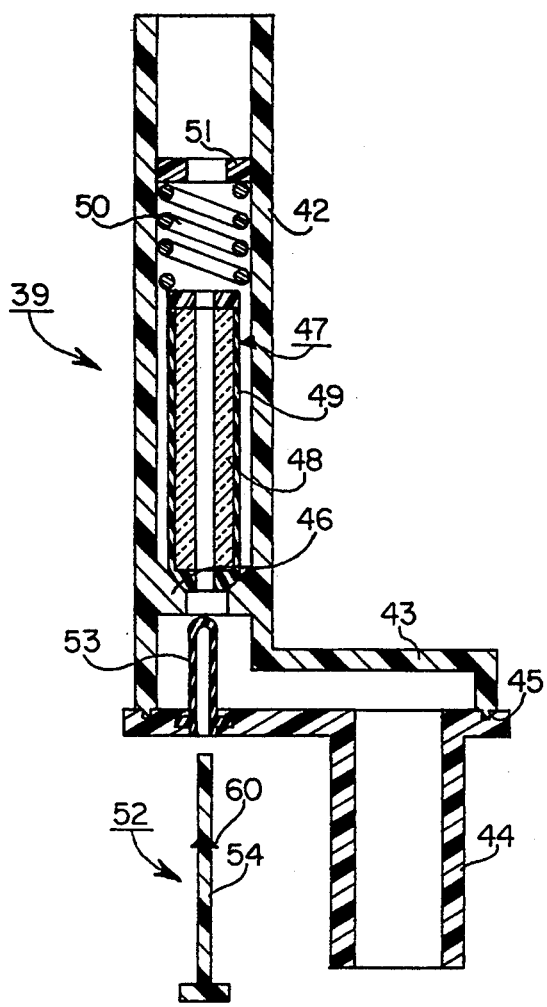
FIG. 4 illustrates a cross-sectional view of a purging and priming device connected between the pump and line of the assembly of FIG. 3.

Referring to FIG. 1, the disposable ambulatory infusion pump assembly 10 includes a pump means 11 for supplying a continuously unrestricted pressurized flow of fluid, a first line 12 in direct communication with the pump means 11 for conveying a pressurized flow of fluid therethrough at a first rate of flow, a second line 13 connected in parallel with the first line 12 for conveying the pressurized flow of fluid from the pump means at a second rate of flow higher than the first rate of flow in the first line 12 and a third line 14 connected in common to the first and second lines 12, 13 in order to receive a flow of fluid from each line. In addition, a connector 15 is connected to the line 14 for discharging the fluid, for example, to a catheter (not shown) in the vein of a patient.

The pump means 11 includes a housing 16, for example, of tubular shape having a pair of end walls 17 to define an enclosed chamber therein. In addition, the pump means 11 includes an inflatable balloon reservoir 18 within the housing 16 for receiving a supply of liquid. As indicated, the housing 16 has a fluid injection port 19 in one end wall 17 which communicates with the balloon reservoir 18 for the passage of fluid into the balloon reservoir 18. For example, fluid may be injected via a syringe or other suitable means into the interior of the balloon reservoir 18.

The housing 16 also includes a fluid discharge port 20 in the opposite end wall which communicates with the balloon reservoir 18 so as to discharge fluid from the balloon reservoir 18 under pressure into a discharge line 21.

The pump means 11 may be constructed in any suitable manner, such as described in U.S. Pat. Nos. 5,080,652, 4,909,790 and 4,904,239, and in particular is constructed so that the balloon reservoir 18 maintains a pressure on the fluid which is discharged through the port 20 into the line 21.

A connector 22 communicates the discharge line 21 with the two fluid-conveying lines 12, 13. In this respect, the connector 22 has an inlet port 23 communicating with the line 21 extending from the pump means 11 in order to receive the flow of fluid therefrom. In addition, a filter 24 is disposed in either the inlet port 23 or the line 21 in order to filter the flow of fluid therethrough.

The connector 22 also has a pair of outlet ports 25, 26 which communicate with the respective lines 12, 13, for example, by receiving each line 12, 13 in telescoping manner. In addition, a restrictor 27 is provided in fixed within either the outlet port 25 or line 12 and within the flow of fluid in order to restrict the rate of flow of fluid through the line 12. For example, the restrictor may be constructed to effect a rate of flow of about 0.5 cubic centimeters per hour in the line 14.

A means, for example, in the form of a clamp 28 is disposed in the second line 13 for selectively opening and closing the line 13 to a flow of liquid therethrough. As indicated, the clamp 28 may be of a type which can be manually manipulated by a patient or technician to open and close the line 13 to a flow of fluid therethrough.

A further connector 29 is connected to the outlet ends of the respective lines 12, 13 and has a pair of inlet ports 30, 31 for receiving the respective lines 12, 13 in telescopic relation. In addition, the connector 29 has an outlet port 32 communicating with the two inlet ports 30, 31 to convey the fluid therethrough into the line 14.

The line 14 is a small diameter tube which provides for a low-fluid hold-up. In the given example, this line may have a diameter of 0.010 inches and a length of 10 inches.

The connector 15 may be in the form of a T-connector having a first inlet port 33 connected to the line 14 to receive a flow of fluid therefrom and a second inlet port in the form of an injection port 34 for receiving a charge of fluids such as a medicament. As indicated, the injection port 34 may have a rubber septum or membrane 35 closing off the port 34. Such a septum 35 may be constructed so as to permit piercing by a hollow needle of a syringe for the injection of medicament into the connector 15 with self-sealing of the septum 35 after removal of the needle.

The connector 15 also has an outlet port, for example, in the form of a male luer connector 36 for connecting to a line (not shown) leading to a catheter implanted in the vein of a patient or directly to the catheter.

In the given example, the balloon reservoir 18 may be constructed of a size to have a dispensing volume of 25 to 30 cubic centimeters of fluid; the line 12 may have a length of 4 inches and an inside diameter of 0.010 inches; the line 13 may have a length of 4 inches and an inside diameter of 0.010 inches; and the line 14 may have a length of 8 inches and an inside diameter of 0.010 inches. Further, the line 13 in conjunction with the other line 14 may function to restrict the flow therethrough to a range of from 1 to 3 cubic centimeters per minute. This range is selected so that the practitioner does not exhaust the fluid supply from the balloon reservoir 18. In this respect, approximately $\frac{1}{8}$ to $\frac{1}{4}$ cubic centimeter is required to flush the line 14, hence, opening the line 13 for from 5 to 15 seconds should be more than adequate to flush the entire system.

In use, at the initial use of the disposable ambulatory infusion pump assembly 10, the connector 15 is connected to a catheter in the vein of a patient or to a female luer connection of a line leading to the catheter. Thereafter, the pump means 11 is actuated or otherwise supplied with fluid so that the balloon reservoir 18 begins to force fluid into a lines 12, 13. With the clamp 28 in a closed position in the line 13, only fluid through the line 12 can pass into the line 14 and connector 15 for discharge to the patient. In this respect, the restrictor 27 is employed to reduce the flow rate through the line 12 to a rate sufficient to keep the vein of the patient open. Such a flow rate may be in the range of about 0.5 cubic centimeters per hour. Since this is a relatively low rate which would take some time to prime, that is, fill the line 14 and connector 15 as well as any line leading to the patient. The clamp 28 is then manipulated so as to open the line 13. The flow through the line 13 is much greater than the flow through the line 12 so that fluid is now able to fill the line 14, connector 15 and the line, if any, leading to the catheter in a minimum of time. Once the line 14 and connector 15 are primed (along with line to the catheter) the clamp is again closed on the line 13 so as to shut off flow through the line 13. From this point on, the pressure in the line 12 is sufficient to supply the fluid into the vein to keep the vein open.

In the event that a charge of medicament is to be given to the patient, a syringe or other suitable instrument can be introduced into the inlet port 34 of the T-connector 15 via the rubber septum 35. After discharge of the medicament into the connector 15, the clamp 28 can again be open so that a flow of fluid from the balloon reservoir 18 can again flow through the line 14 and connector 15 to flush out any remaining medicament in the connector 15 as well as in the line (not shown) leading to the catheter. The time of opening of the clamp may be momentary or somewhat prolonged in order to ensure a complete flushing of the medicament into the vein of the patient. Thereafter, the clamp 28 is again closed on the tube 13.

Referring to FIG. 2, wherein like reference characters indicate like parts as above, the means in the line 13 for selectively opening and closing the line 13 may include a one way valve 37 and an inflatable reservoir 38 upstream of the valve 37. As indicated, the valve 37 may be formed so as to prevent flow to the downstream end of the tube 13. For example, the valve 37 is formed of a conical shaped member which has an opening at the apex which is closed when the valve 37 is in the closed position. The inflatable reservoir 38 may be in the form of a bulge in the line 13 which can be filled with fluid from the upstream end of the line 13. The reservoir 38 is collapsible under an externally applied collapsing force so as to effect opening of the valve 37. In this respect, the patient or technician may squeeze down on the reservoir 38 causing the conically shaped valve 37 to open. That is, the valve 37 and reservoir 38 are made of an integral one-piece structure so that as the reservoir 38 flattens, the conical wall of the valve 37 tends to splay radially outwardly thereby providing an opening at the apex to permit a flow of fluid therethrough. Such a composite valve 37 and reservoir 38 structure can be made, for example, of plastic or rubber.

Once the reservoir 38 has been squeezed into a flattened condition, the fluid flows through the valve 37 for dispensing into the patient. Upon release of the externally applied force, the reservoir expands to the shape as indicated in FIG. 2 thereby causing the valve 37 to close. This shuts off the flow of fluid to the line 13. Fluid then continues to flow through the line 12 in which the restrictor 27 is positioned so as to keep the vein of the patient opened under a reduced rate of flow.

Referring to FIG. 3, wherein like reference characters indicate like parts as above as above, the disposable ambulatory infusion pump assembly 38 includes a pump means 11 for supplying a pressurized flow of fluid, a purging/priming device 39 for controlling the flow of fluid from the pump 11, a line 14 connected to the purging and priming device 39 to receive a flow of fluid therefrom and a Y-site connector 15 connected to the line 14 for discharging the fluid. As indicated, the connector 15 has an outlet connected with a line 40 which, in turn, leads to a luer-type connector 41 of known construction, for example for connection to a catheter disposed in a vein of a patient.

Referring to FIGS. 3 and 4, the purging and priming device 39 includes a cylindrical tube 42, a fluid channel 43 perpendicular to the tube 42 to receive a flow of fluid therefrom and a stub tube 44 perpendicular to the channel 43 to receive a flow of fluid therefrom. As indicated, the channel 43 may have one portion integral with the cylindrical tube 42 and a second portion which is integral with the stub tube 44 wherein the two portions are snap fitted or otherwise connected to each other through a suitable connection 45. The connection 45 is such as to permit the tube 44 to be disconnected from the cylindrical tube 42 for assembly or cleaning purposes.

Referring to FIG. 4, the cylindrical tube 42 defines a line in communication with the pump means 11 to receive a pressurized flow of fluid and includes a restricted portion 46 which defines a valve seat. In addition, a restrictor 47 in the form of a hollow glass tube 48 encased in a hollow rubber valve body or sleeve 49 is disposed in spaced concentric relation to the tube 42 and coaxially of the valve seat 46 with one end coaxially seated on the valve seat 46 in sealing relation. As indicated, the glass tube 48 has a bore which is of the same size as openings at each end of the valve body 49 to convey the fluid. In addition, a spring 50 is disposed within the cylindrical tube 42 to bias the restrictor 47 into sealing relation with the valve seat 46 so as to block a flow of fluid from about the restrictor 47 through the valve seat 46 while allowing a flow of fluid through the restrictor 47 and the valve seat 46. As indicated, a suitable plug washer 51 or the like is provided to secure the spring 50 in place within the cylindrical tube 42.

The restrictor 47 is thus disposed in the line defined by the cylindrical tube 42 for restricting the rate of fluid flow through the tube 42 while the portion of the line 42 about the restrictor 47 is in parallel with the restrictor 47 to convey a flow of fluid from the pump means 11 to the connector 15 at an unrestricted rate of flow relative to the rate of flow through the restrictor 47.

A means is also provided in the device 38 for selectively opening and closing the second portion of the line 42, that is, the portion surrounding the restrictor 47 to convey a flow of fluid to the connector 15. As indicated, this means is in the form of a valve actuator 52 for moving the restrictor 47 away from the valve seat 46 in a direction towards the spring 50. The valve actuator 52 includes an expandable sleeve 53, for example, of an elastomeric material which is mounted in an opening in the channel 43 with a closed end facing and coaxially of the valve seat 46 and restrictor 47. The valve actuator also has a pin 54 which is removably mounted in the sleeve 53. As indicated, the pin 54 is of a length so as to elongate the sleeve 53 when pushed into the sleeve 53 in order to elongate the sleeve 53 into contact with the restrictor 47 so as to move the restrictor 47 from the valve seat 46. This permits the flow of fluid to pass from about the restrictor 47 through the valve seat 46. At the same time, the sleeve 53 is brought into sealing engagement with the bore of the valve body 49 of the restrictor 47 so as to prevent a flow of fluid therethrough.

As shown in FIG. 4, the sleeve 53 is held in the portion of the channel 43 integral with the tube 44 via an integral flange which fits into an annular recess of the channel 43. In addition, the rubber valve body 49 disposed about the glass tube 50 facilitates sealing of the restrictor 47 against the valve seat 46, while providing a surface against which the spring 48 may press.

Figure 5:
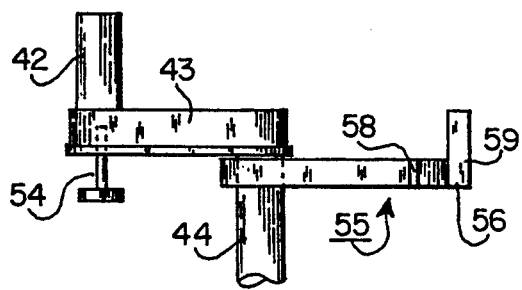
FIG. 5 illustrates a view of a locking means for guarding against inadvertent actuation of the purging and priming device.
Figure 6:
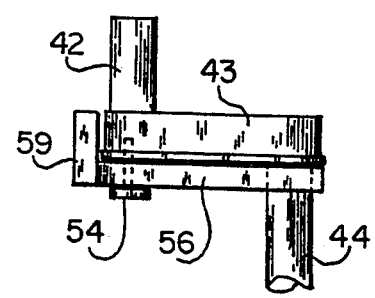
FIG. 6 illustrates a view of the locking device in a closed safety position.

Referring to FIGS. 3, 5 and 6, a locking means 55 is mounted on the fluid channel 43 of the purging and priming device 39 for guarding against inadvertant actuation of the device 39. This locking means 55 may be in the form of a lever 56 which is pivotally mounted about the tube 44. For example, the lever 56 has a hooked end which is snap-fitted into an annular groove in the tube 44 to rotate about the axis of the tube 44. In addition, the lever 56 includes a groove 58, for example, of semi-cylindrical shape for receiving a stem of the pin 54 so that when the lever 56 is positioned as indicated in FIG. 6 in a locking position, the pin 54 cannot be pushed into the device 39 to move the restrictor 47 from the valve seat 46. The groove 58 may also be shaped so as to releasably engage the stem of the pin 54 so that the pin 54 cannot be withdrawn from the sleeve 53. When the lever 56 is moved into the release position as shown in FIG. 5, the pin 54 is free to be depressed into the device 39.

As indicated in FIG. 6, the lever 56 has a depending portion 59, as viewed, to slidably engage about the channel 43 so as to be retained in a fixed position relative to the device 39. The connection between the depending portion 59 and the channel 43 should be such as to permit manual release of the lever 56 for pivoting into the open position as shown in FIG. 5.

Referring to FIG. 4, the pin 54 may be provided with a nib or small bar 60 at an intermediate point of the stem to secure the pin 54 in the elastomeric sleeve 53 to an extent sufficient to prevent an inadvertant falling out of the pin 54, for example, under gravity.

The disposable ambulatory infusion pump assembly 38 may be used in similar fashion to the above embodiments. In this respect, with the restrictor 47 in the position as shown in FIG. 4, a restricted flow of fluid is passed through the line 14 into the connector 15 and, thence, through the line 40 and connector 41 to the patient in order to keep a vein open. In order to purge the line 14 or to prime the line 14, the pin 54 is placed in the sleeve 53 of the device 38 and pushed inwardly so as to push the restrictor 47 from the valve seat 46, This permits the flow of fluid from the pump means 11 to flow about the restrictor 47 through the valve seat 46 into the channel 43, and the stub tube 44 into the line 14. The size of the restrictor 47 and any covering thereon relative to the cylindrical tube 42 is such that the flow rate about the restrictor 47 is much greater than the flow rate through the bore of the restrictor 47.

For priming and/or purging uses, the restrictor tube 47 is manually pushed away from valve seat 46 thereby allowing a significantly higher rate of flow, for example, from 2 to 10 cubic centimeters per minute. This rate of flow is sufficient to prime or purge the line 14 in from 2 to 15 seconds which is ample time for the practitioner to depress the valve pin 54 before releasing the pin 54 into a "keep catheter patent mode."

After the pin 54 has been used to prime or purge the line 14, the pin 54 may be removed in order to prevent accidental depressing of the pin 54 by a patient.

The components of the infusion pump assembly are relatively simple. Accordingly, the infusion pump assembly can be readily fitted to a patient, particularly an ambulatory patient. Further, depending upon the amount of fluid required, the overall pump size can be relatively compact as well as light in weight.

The operation of the pump assembly is relatively simple and does not require complex or cumbersome parts to manipulate on the part of the patient. Further, a bolus or charge of medicament or other type of fluid can be readily injected into the T-connector of the pump assembly in order to provide the patient with the medicament in an easy and dose-controlled manner.

The invention further provides a pump assembly in which two lines can be provided to give a controlled very low flow through one line and a much higher flow through the second line for priming the pump assembly and/or for purging residual medication after drug delivery from the pump assembly.

What is claimed is:

1. A disposable ambulatory infusion pump assembly for delivering fluid intravenously to a patient comprising
   a pump means for supplying a continuous unrestricted pressurized flow of fluid;
   a first line in direct communication with said pump means for conveying the pressurized flow of fluid therethrough;
   a restrictor fixed within one portion of said line and within the flow of fluid for restricting the rate of the flow of fluid through said line;
   a connector having a first inlet port in communication with said line to receive the flow of fluid therefrom and having an outlet port for connection to a catheter in a patient;
   a second line connected in parallel with said portion of said first line to convey a flow of fluid from said pump means to said inlet port of said connector at an unrestricted rate of flow relative to said rate of flow in said first line; and
   means in said second line for selectively opening and closing said second line to a flow of fluid therethrough.

2. An assembly as set forth in claim 1 wherein said pump means includes a housing and an inflatable balloon reservoir in said housing for receiving a supply of liquid, said reservoir being connected to said first line to deliver a pressurized flow of liquid thereto.

3. An assembly as set forth in claim 2 wherein said pump means includes a fluid injection port in said housing communicating with said balloon reservoir for passage of fluid into said balloon reservoir.

4. An assembly as set forth in claim 1 wherein said restrictor effects a rate of flow of about 0.5 cubic centimeters per hour in said first line.

5. An assembly as set forth in claim 1 wherein said connector includes a second inlet port in communication with said outlet port for receiving a second flow of fluid for discharge through said outlet port.

6. An assembly as set forth in claim 1 wherein said means in said second line is a manually operated clamp.

7. An assembly as set forth in claim 1 wherein said means in said second line includes a one way valve and an inflatable reservoir upstream of said valve for receiving fluid therein, said reservoir being collapsible under an externally applied collapsing force to effect opening of said valve.

8. A disposable ambulatory infusion pump assembly for delivering fluid intravenously to a patient comprising
   a pump means for supplying a pressurized flow of fluid;
   a first connector having an inlet port communicating with said pump means to receive a flow of fluid therefrom, a first outlet port communicating with said inlet port and a second outlet port communicating with said inlet port;
   a first line extending from said first outlet port for conveying a flow of fluid at a first rate of flow therethrough;
   a second line extending from said second outlet port for conveying a flow of fluid at a second rate of flow higher than said first rate of flow;
   means in said second line for selectively opening and closing said second line to a flow of fluid therethrough;
   a second connector having a pair of inlet ports communicating with said respective first and second lines and an outlet port communicating with said pair of inlet ports;
   a third line extending from said outlet port of said second connector; and
   a third connector having an inlet port connected to said third line to receive a flow of fluid therefrom and an outlet port for discharging the flow of fluid therefrom.

9. An assembly as set forth in claim 8 which further comprises a restrictor in said first line to effect said first rate of flow.

10. An assembly as set forth in claim 9 wherein said means in said second line is a manually operated clamp.

11. An assembly as set forth in claim 9 wherein said means in said second line includes a one way valve and an inflatable reservoir upstream of said valve for receiving fluid therein, said reservoir being collapsible under an externally applied collapsing force to effect opening of said valve.

12. An assembly as set forth in claim 8 wherein said third connector includes a second inlet port for receiving a charge of medicament, said second inlet port being in communication with said outlet port of said third connector to discharge the medicament therethrough.

13. A disposable ambulatory infusion pump assembly for delivering fluid intravenously to a patient comprising a pump means for supplying a continuous unrestricted pressurized flow of fluid;

a first line in direct communication with said pump means for conveying the pressurized flow of fluid therethrough at a first rate of flow;

a second line connected in parallel with said first line for conveying a flow of fluid from said pump means at a second rate of flow higher than said first rate of flow;

a third line connected in common to said first and second lines to receive a flow of fluid from each said line;

a connector having an inlet port connected to said third line to receive a flow of fluid therefrom and an outlet port communicating with said inlet port to discharge fluid; and means in said second line for selectively opening and closing said second line to a flow of liquid therethrough whereby with said means opening said second line, a flow of fluid is passed through said connector to prime said third line.

14. An assembly as set forth in claim 13 wherein said connector includes a second inlet port for receiving a dose of a second fluid, said second inlet port being in communication with said outlet port and wherein with said means opening said second line, a flow of fluid is passed through said connector to flush the second fluid from said outlet port of said connector.

* * * * *